(12) United States Patent
Bragulla et al.

(10) Patent No.: US 6,683,040 B2
(45) Date of Patent: Jan. 27, 2004

(54) PERACIDS WITH GOOD ADHESION TO SURFACES

(75) Inventors: Siegfried Bragulla, Monheim (DE); Alfred Laufenberg, Dormagen (DE); Harald Kluschanzoff, Mettmann (DE)

(73) Assignee: Ecolab GmbH & Co. oHG, Dusseldorf (DE)

( * ) Notice: Subject to any disclaimer, the term of this patent is extended or adjusted under 35 U.S.C. 154(b) by 126 days.

(21) Appl. No.: 10/168,612

(22) PCT Filed: Dec. 14, 2000

(86) PCT No.: PCT/EP00/12689

§ 371 (c)(1), (2), (4) Date: Jun. 24, 2002

(87) PCT Pub. No.: WO01/47359

PCT Pub. Date: Jul. 5, 2001

(65) Prior Publication Data

US 2003/0133956 A1 Jul. 17, 2003

(30) Foreign Application Priority Data

Dec. 23, 1999 (DE) .......................................... 199 62 342

(51) Int. Cl.$^7$ ............................ C11D 3/395; C11D 7/54; C11D 17/00; C11D 3/00; C11D 7/18

(52) U.S. Cl. ...................... 510/375; 510/372; 510/433

(58) Field of Search ................................. 510/372, 375, 510/433

(56) References Cited

U.S. PATENT DOCUMENTS

| | | | |
|---|---|---|---|
| 5,200,189 A | | 4/1993 | Oakes et al. |
| 5,733,474 A | * | 3/1998 | Kagermeier et al. ... 252/186.25 |
| 5,962,392 A | * | 10/1999 | Revell et al. ................ 510/372 |
| 6,008,405 A | * | 12/1999 | Gray et al. .................... 562/3 |
| 6,274,542 B1 | * | 8/2001 | Carr et al. .................. 510/376 |

FOREIGN PATENT DOCUMENTS

| | | |
|---|---|---|
| DE | 42 28 786 | 3/1994 |
| DE | 43 31 942 | 2/1996 |
| DE | 196 39 603 | 4/1998 |
| DE | 695 08 939 | 11/1999 |
| EP | 0 765 309 | 4/1997 |
| GB | 1 566 671 | 5/1980 |
| WO | WO 92/19287 | 11/1992 |
| WO | WO 95/34537 | 12/1995 |
| WO | WO 98/28267 | 7/1998 |

* cited by examiner

Primary Examiner—Charles Boyer
Assistant Examiner—John M. Petruncio
(74) Attorney, Agent, or Firm—Merchant & Gould P.C.

(57) ABSTRACT

The present invention relates to the use of peracid esters for improving surface wetting during the disinfection of surfaces and to synergistic antimicrobial combinations of peracid esters with further components.

3 Claims, No Drawings

PERACIDS WITH GOOD ADHESION TO SURFACES

The present invention relates to the use of peracid esters for improving surface wetting during the disinfection of surfaces and to synergistic antimicrobial combinations of peracid esters with further components.

It is known in the state of the art that peracid compounds, for example peracetic acid, can be used for disinfecting surfaces. Peracid compounds are very effective biocides. However, most peracids have an unpleasant odor, particularly when they are used in systems where people are exposed to the unpleasant odor.

It was therefore desirable to find alternative disinfecting ingredients. As disinfecting ingredients with an oxidative action mechanism can usually destroy germs within a short period of time, these ingredients could readily be used for disinfecting surfaces. The alternatives to peracid disinfecting ingredients with an oxidative action mechanism known in the state of the art, such as hypochlorite, ozone, chlorine dioxide, also have drawbacks in use, for example unpleasant odor, formation of ecotoxic compounds which may pollute the waste water, formation of gases which may be toxic to humans and difficult handling, production and stability.

The patent EP 765 309 relates to aqueous peracid ester solutions which are stable in storage and to the use thereof as disinfectants. According to the cited patent, these peracid ester solutions have less odor than the aliphatic $C_1$ to $C_3$ peracids conventionally used.

As a result, peracid ester solutions of this type can be used in areas where peracids were formerly avoided owing to their unpleasant odor.

The cited document therefore teaches us that the odor problem associated with conventional peracids can be solved by using peracid esters.

However, the document fail to mention that conventional peracids have a further serious drawback. The peracids conventionally used for disinfection have only low affinity with surfaces, which means that, when they are used in disinfecting processes, the disinfecting solutions adhere-to the surfaces to be treated only for a short time and then drip onto the floor or run off the surface to be treated. This rapid dripping or running means that the peracid solution has only a short period of contact with the surfaces to be treated and this adversely affects the resultant disinfection. To achieve optimum disinfection, it is desirable to lengthen the time for which the disinfecting ingredient is in contact with the surface to be treated. To achieve this object, surface-wetting aids are added in practice, for example during aseptic decanting. The preferred surface-wetting aids often lead to unstable formulations with peracid compounds. Furthermore, additional aids should be considered only as additional ballast in many cases, from the economic, ecological and toxicological points of view. There was therefore a need for oxidatively acting ingredients which, considered per se, wet surfaces better.

It was accordingly the object of the present invention to look for peracid compounds which have a particularly advantageous influence on the adhesion to and/or the wetting of surfaces in use.

The present invention relates to use of formulations containing at least one peracid ester of general formula

$$R-O_2C-(CH_2)_x-CO_3H$$

wherein R is an alkyl group containing 1 to 4 carbon atoms wherein it is preferred if R is a methyl group, and x is a number from 1 to 4, wherein it is particularly preferred if the formulations contain one or more peracid esters selected from persuccinic acid monomethyl ester, perglutaric acid monomethyl ester, peradipic acid monomethyl ester, and the formulation preferably contains 0.001 to 15% by weight, particularly preferably 0.1 to 5% by weight of one or more peracid esters, based on the total formulation, for achieving better surface welting with formulations of this type than with identical molar amounts of the corresponding peracids alone or combined with mole-equivalent amounts of the corresponding alcohol during the disinfecting and/or cleaning of surfaces. Preferably, with the use according to the invention there is a longer contact time between the formulations to be used according to the invention and the surface or surfaces which are not arranged horizontally when using identical molar amounts of the corresponding peracids alone or combined with mole-equivalent amounts of the corresponding alcohol. It is also preferred that a better antimicrobial and/or additional cleaning effect is achieved with use according to the invention than with the use of identical molar amounts of the corresponding peracids alone or in combination with mole-equivalent amounts of the corresponding alcohol. In a further preferred embodiment of the use according to the invention, it is possible, with a lower concentration and/or reduced unpleasant odor to achieve at least the same antimicrobial activity as when using identical molar amounts of the corresponding peracids alone or combined with mole-equivalent amounts of the corresponding alcohol.

It is also preferred if the formulations to be used according to the invention additionally contain 1 to 50% by weight of hydrogen peroxide, based on the total formulation.

Furthermore, it is preferred if the formulations to be used according to the invention additionally contain 0.1 to 25% by weight of at least one non-esterified peracid, based on the total formulation, and it is particularly preferred if a peracid selected from monoperoxycarboxylic acids and/or diperoxydicarboxylic acids is contained as non-esterified peracid, and it is quite particularly preferred if the non-esterified peracids present in the formulations used according to the invention are selected from peracetic acid, perpropionic acid, persuccinic acid, perglutaric acid, peradipic acid, (ω-phthalimidoperoxyhexanic acid, fatty peracid containing 8 to 18 carbon atoms per molecule or mixtures of the aforementioned peracids.

In a further preferred embodiment of the present invention, the formulation to be used according to the invention additionally contains 5 to 50% by weight of at least one organic acid, based on the total formulation, which is not a peracid and is preferably selected from acetic acid, propionic acid, succinic acid, glutaric acid, adipic acid, (o-phthalimidoperoxyhexanic acid, fatty acids containing 8 to 18 carbons atoms per molecule or mixtures of these acids.

It is also preferred if the formulation to be used according to the invention additionally contains at least one hydrotrope, and it is particularly preferred if the hydrotrope used is selected from the group consisting of anionic surfactants, quite particularly preferably from sulfonates/sulfonic acids and, in particular, from cumene, xylene, octyl, naphthyl and alkylbenzene sulfonates/sulfonic acids, the alkyl group containing between 6 and 16 carbon atoms in the last case, or mixtures of these compounds and/or further compounds which may be suitable as solubilizers for longer chain peracids.

It is also preferred if the formulations to be used according to the invention additionally contain at least one component with complexing properties for polyvalent metal ions. The formulations to be used according to the invention particularly preferably contain, as component with complexing properties, a compound selected from nitrilotriacetic acid, ethylenediamine tetraacetic acid, methylglycine diacetic acid, gluconic acid, citric acid, dicarboxymethyl-L-glutamic acid, serine diacetic acid, imidosuccinic acid, the polycarboxylic and phosphonic acid group and the respective salts thereof.

Examples of polycarboxylic acids include polyacrylic acids and copolymers of maleic acid anhydride and acrylic acid as well as the sodium salts of these polymeric acids. Conventional commercial products include Sokalan® CP 5 and PA 30 made by BASF, Alcosperse® 175 and 177 made by Alco, LMW® 45 N and SPO2 ND made by Norsohaas Suitable native polymers include oxidized starch (for example, DE 42 28 786) and polyamino acids such as polyglutamic acid or polyaspartic acid made by Cygnus, Bayer, Rohm & Haas, Rhône-Poulenc or SRCHEM, for example.

Examples of phosphonic acids include 1-hydroxyethane-1,1-diphosphonic acid, diethylenetriamine pentamethylene phosphonic acid or ethylenediamine tetramethylene phosphonic acid and the alkali salts thereof.

In a particularly preferred embodiment of the present invention, the peracid esters in the formulations to be used according to the invention form, together with
a) at least one fatty acid preferably containing 8 to 12 carbon atoms, the fatty acid particularly preferably being octanic acid and/or
b) at least one hydrotrope which is particularly preferably cumene, octyl, naphthyl, xylene or alkylbenzenesulfonate containing 4 to 16 carbon atoms in the alkyl group
c) at least one surfactant foam carrier component which is preferably an amine oxide derivative which is stable to oxidizing agents, and it is particularly preferred if the amine oxide derivative is a trialkyl amine oxide with an alkyl group containing 8 to 20 carbon atoms and two alkyl groups containing a smaller number of carbon atoms in the alkyl chain, wherein the two shorter alkyl groups can be the same or different and it is particularly preferred if the amine oxide derivative is tallow grease-bis-(2-hydroxyethyl-)-amine oxide, oleyl-bis-(2-hydroxyethyl-)-amine oxide, coconut-bis-(2-hydroxyethyl-)-amine oxide, tetradecyidimethyl-amine oxide and/or alkyldimethyl-amine oxide, containing 12 to 18 carbons atoms in the alkyl chain
an antimicrobial, synergistically acting composition and/or a sudsing combination for the cleaning and/or disinfecting of surfaces.

Additional preferred surfactant additives to formulations to be used according to the invention are selected from the groups consisting of anionic, cationic, nonionic, amphoteric surfactants, protein hydrolysates, alkylamine oxides, silicone compounds and phosphoric acid esters and salts thereof.

Suitable anionic surfactants include any conventional anionic surfactants in the field of detergents and cleaning agents which can also act as a hydrotrope, as mentioned above, for example $C_8$–$C_{18}$ alkylsulfates, $C_8$–$C_{18}$ alkylethersulfates, $C_8$–$C_{18}$ alkanesulfonates, $C_8$–$C_{18}$-α-olefin sulfonates, sulfonated $C_8$–$C_{18}$ fatty acids, $C_8$–$C_{18}$ alkylbenzenesulfonates, sulfosuccinic acid mono- and di-$C_1$–$C_{12}$ alkyl esters, $C_8$–$C_{18}$ alkylpolyglycolether carboxylates, $C_8$–$C_{18}$ N-acyltaurides, $C_8$–$C_{18}$ N-sarcosinates, $C_8$–$C_{18}$ alkylisothionates and mixtures thereof.

The nonionic surfactants in the formulations to be used according to the invention are preferably alkylpolyglucosides which can normally be obtained industrially by condensation of fatty alcohols with glucose or polyglucose and are commercially available in various forms. Examples of alkylpolyglucosides which are particularly suitable for the use according to the invention include the products Glucopon® 600 made by Henkel and Triton® BG10 made by Rohm & Haas.

Further preferred nonionic surfactants include alkoxylated alkyl alcohols containing 8 to 22 carbon atoms in the alkyl chain wherein, in particular, at least one compound consisting of the groups of mixed ethoxylates/propoxylates of branched or unbranched alkyl alcohols containing 8 to 22 carbon atoms in the alkyl chain and the ethoxylates comprising terminal groups, of branched or unbranched alkyl alcohols containing 8 to 22 carbon atoms in the alkyl chain is contained, and quite particularly preferably at least one compound from the groups consisting of ethoxylated and propoxylated alkyl alcohols containing 12 to 22 carbon atoms in the alkyl part, the butyl ethers of ethoxylated alkyl alcohols containing 12 to 22 carbon atoms in the alkyl part and methyl ethers of ethoxylated alkyl alcohols containing 12 to 22 carbon atoms in the alkyl part, butyl ether and methyl ether of the ethoxylated 2-octyl-1-dodecanol being contained in the specific case. Nonionic surfactants which are particularly suitable for producing the formulations according to the invention include, for example, Plurafac® LF 403, Plurafac® 431 made by BASF and Dehypon® LT 104 and Dehypon® G 2084 made by Henkel.

Phosphoric acid ester compounds, preferably including at least one salt of a phosphoric acid partial ester, are preferably used as phosphoric acid ester in the formulations to be used according to the invention, at least one alkali salt of a phosphoric acid partial ester of alkoxylated alkyl phenol particularly preferably being used.

Phosphoric acid esters are surfactant substances preferably derived from long-chain aliphatic or araliphatic alcohols. Salts of phosphoric acid partial esters have proven particularly suitable, in particular the salts of alkoxylated alkyl phenols in this case. Sodium and potassium salts are preferably used as alkali salts, the potassium salts being particularly preferred. Surfactant phosphoric acid partial esters of the type which are preferably used according to the invention are commercially available. An example of an active ingredient of this type which is particularly suitable according to the invention is the product Triton® H 66 (Rohm & Haas).

It is preferred if the formulations are in the form of an aqueous solution, gel, emulsion, paste, dispersion, powder, granulate, flakes, pearls, tablets, block-like shaped bodies or extrudate:

It is also preferred if the formulations to be used according to the invention are diluted with water, if necessary, prior to use for cleaning and/or disinfecting purposes, and it is particularly preferred if the dilution factor is between 10 and 10000.

Preferably, the formulations to be used according to the invention are applied in concentrated form or diluted with water to the surfaces to be treated by immersion and/or by aids which can be selected from paintbrushes, sponges, rollers, cloths, rags, brushes, wipers, rubber, mops, is flat wipe covers or sprayers, and it is particularly preferred if aqueous, gel, foam, suspension, emulsion or paste-like filming takes place on the surface to be treated and the formulations to be used according to the invention have rheopexic or thixotropic properties, if necessary.

It is also preferred if the formulations to be used according to the invention are used as combined cleaning compositions and disinfectants, and it is particularly preferred if the formulations to be used according to the invention are used for the cleaning and/or disinfecting of surfaces which contain materials selected from plastics materials, textile fibers, glass, ceramic, porcelain, quartz, granite, metal and wood as main constituents.

It is preferred if animal hooves, skin, crockery, textiles, tiles, walls, floor coverings, wood and stone surfaces, floors and walls, work surfaces, external surfaces of machinery, small parts of machines, medical instruments and/or apparatus, coated and/or uncoated tanks and/or other containers, pipes, conveyor belts, drums, foods such as fruit and vegetables are cleaned and/or disinfected with the formulations to be used according to the invention. It is particularly preferred if the formulations to be used according to the invention are used for disinfecting reusable and disposable containers made of glass, cardboard and/or plastics material.

A preferred special application of the formulations to be used according to the invention is in the course of the aseptic or low-germ decanting of microbiologically sensitive foods, in particular of iced tea, apple juice with mineral water, alcoholic and/or alcohol-free beer, milk or yogurt, and it is particularly preferred if the food packaging is treated with formulations to be used according to the invention prior to decanting of the microbiologically sensitive products and/or the surfaces in the low-germ decanting region, including the food-carrying pipes, tanks, devices, machines, conveyor belts and equipment, rinsers and production devices for the containers are treated with formulations to be used according to the invention.

The formulations to be used according to the invention are accordingly preferably used in the household, in the food-manufacturing and processing industry, for example in the drinks, dairy and fish industry and in the butcher's trade as well as in catering establishments, in the cleaning of buildings, for example by professional services, in hospitals, in industrial laundries and in agriculture.

The present invention also relates to antimicrobial, synergistically acting composition for the cleaning and disinfecting of surfaces containing at least one peracid ester of general formula

wherein R is an alkyl group containing 1 to 4 carbon atoms and x is a number from 1 to 4, combined with a component selected from
a) at least one fatty acid containing 8 to 18 carbon atoms, preferably 8 to 12 carbon atoms, the fatty acid particularly preferably being octanic acid and/or
b) at least one hydrotrope which is preferably selected from cumene sulfonate, octyl sulfonate, naphthyl sulfonate, xylene sulfonate or mixtures of these compounds and other solubilizers which are suitable as solubilizers for longer chain peracids and/or
c) at least one surfactant foam carrier component which is preferably an amine oxide derivative which is stable to oxidizing agents, and it is particularly preferred if the amine oxide derivative is a trialkyl amine oxide with an alkyl group containing 8 to 20 carbon atoms and two alkyl groups with a smaller number of carbon atoms in the alkyl chain, wherein the two shorter alkyl groups can be the same or different and it is particularly preferred if the amine oxide derivative is tallow grease-bis-(2-hydroxyethyl-)-amine oxide, oleyl-bis-(2-hydroxyethyl-)-amine oxide, coconut-bis-(2-hyd roxyethyl-)-amine oxide, tetradecyldimethyl-amine oxide and/or alkyldimethyl-amine oxide, containing 12 to 18 carbons atoms in the alkyl chain.

The antimicrobial, synergistically acting composition preferably contains, based on the total formulation, 0.0001 to 15% by weight, particularly preferably 0.1 to 5% by weight, of one or more peracid esters and 0.01 to 15% by weight, particularly preferably 1 to 10% by weight, of at least one fatty acid and/or 0.01 to 25% by weight, particularly preferably 1 to 15% by weight, of at least one hydrotrope and/or 0.01 to 15% by weight, particularly preferably 1 to 10% by weight of at least one surfactant foam carrier component, the preferred embodiments of the fatty acids, hydrotropes and surfactant foam carrier components already having been mentioned in the text. The claimed antimicrobial, synergistically acting compositions are preferably used in the applications previously described in the text.

It is quite particularly preferred if the synergistically antimicrobially acting compositions contain additional activity-increasing anionic surfactants such as alkylbenzenesulfonic acid or salts thereof or further alkyl sulfonic acids or salts thereof.

Effects going beyond this are achieved in special synergistically acting compositions, if the compositions according to the invention are combined with other peracids, for example ω-phthalimidoperoxyhexanic acid.

EXAMPLES

Example 1:

The runoff behavior of various peracid solutions is examined in a test.

Formulations P1, P2, P3 and P4, which differ only in the type and quantity of peracid used are used in a 5% aqueous solution and in the form of the concentrate as a starting point for the tests. The ingredients of these formulations are shown in Table 1.

TABLE 1

| Peracid compositions P1, P2, P3, P4 for the tests on the runoff behavior | | | | |
|---|---|---|---|---|
| Peracid content | P1 | P2 | P3 | P4 |
| Perglutaric acid monomethyl ester (10%) | 100 | — | — | — |
| Peracetic acid (10%) | — | 100 | — | — |
| Perglutaric acid (10%) | — | — | 100 | 90 |
| Methanol | — | — | — | 10 |

200 ml of the peracid formulations P1, P2, P3 and P4 in each case are placed in 250 ml beakers as 5% aqueous solution and in the form of the concentrate.

Previously degreased and weighed stainless steel sheets are then immersed into these solutions.

In the next stage, the sheets are removed from the solutions using forceps.

The remaining solution is allowed to run off for 10 seconds, and the sheets are then weighed again. The residual amount on the sheets, determined in this way, is a criterion for the affinity of the test solution to the surface or for the adhesion to the surface.

Table 2 gives a summary of the adhering amounts determined in this way.

TABLE 2

Residual amounts adhering to the sheets as a function of the peracid formulation in concentrated form or in a 5% aqueous solution

|                       | P1  | P1 5% | P2  | P2 5% | P3  | P3 5% | P4  | P4 5% |
|-----------------------|-----|-------|-----|-------|-----|-------|-----|-------|
| Amounts adhering, in mg | 365 | 141   | 231 | 121   | 264 | 125   | 260 | 126   |

It is found that the peracid ester formulations to be used according to the invention have better wetting or affinity to surfaces than the corresponding comparison formulations.

Example 2

The anti-microbial activity of various combinations of peracid esters with selected additives was investigated in DVG's quantitative suspension test.

*Staphylococcus aureus* and *Escherichia coli* were used as test germs for determining the bactericidal activity. *Saccharomyces cerevisiae* and *Aspergillus niger* were used as test germs for determining the fungicidal activity. The formulations tested are contained in Table 1. Table 2 and Table 3 show the results of the quantitative suspension test.

TABLE 1

Formulations for the microbiological experiment

| Raw material | Form. 1 | Form. 2 | Form. 3 | Form. 4 | Comparison form. |
|---|---|---|---|---|---|
| Perglutaric acid monomethyl ester (10%) | 80 | 80 | 80 | 80 | 100 |
| Alkylbenzene-sulfonic acid | 10 | — | — | 10 | — |
| Dimethylcoconut-amine oxide | — | 10 | — | — | — |
| Sodium octyl sulfonate | — | — | 16 | 6 | — |
| Octanic acid | — | — | 4 | 4 | — |
| Water | 10 | 10 | — | — | — |

TABLE 2

Results of the microbiological experiments against bacteria

| | | *Staphylococcus aureus* ATCC 6538 (K 3212) Inoculum 7.05 × 10$^8$ KBE/ml | | *Escherichia coli* ATCC 10536 (K 2124) Inoculum 1.07 × 10$^9$ KBE/ml | |
|---|---|---|---|---|---|
| Product | [AWK] % | 1 minute RF | 5 minutes RF | 1 minute RF | 5 minutes RF |
| Comparison | 0.1 | 0.04 | >4.87 | 3.69 | >5.3 |
| Formulation | 0.3 | 0.59 | >4.87 | >5.2 | >5.3 |
| Formulation 1 | 0.1 | 3.42 | >4.87 | >5.2 | >5.3 |
| | 0.3 | >4.9 | >4.87 | >5.2 | >5.3 |
| Formulation 2 | 0.1 | 0 | 0.09 | 1.17 | >5.3 |
| | 0.3 | 0.03 | >4.87 | >5.2 | >5.3 |
| Formulation 3 | 0.1 | >4.9 | >4.87 | >5.2 | >5.3 |
| | 0.3 | >4.9 | >4.87 | >5.2 | >5.3 |
| Formulation 4 | 0.1 | 3.04 | >4.87 | >5.2 | >5.3 |
| | 0.3 | >4.9 | >4.87 | >5.2 | >5.3 |

AWK = concentration used; RF values = germ reduction in LOG stages

TABLE 3

Table of results for DVG fungicidal activity

| | | *Saccharomyces cerevisiae* ATCC 9763 (K 5011) Inoculum 1.36 × 10$^7$ KBE/ml | | *Aspergillus niger* ATCC 16404 (K 7444) Inoculum 1.07 × 10$^9$ KBE/ml | |
|---|---|---|---|---|---|
| Product | [AWK] % | 5 minutes RF | 30 minutes RF | 5 minutes RF | 30 minutes RF |
| Comparison | 0.3 | 0.21 | 0.24 | 0 | 0 |
| formulation | 1.0 | 0.24 | 1.1 | 0 | 0 |
| Formulation 1 | 0.3 | 2.88 | >3.19 | 0 | 0 |
| | 1.0 | >3.18 | >3.19 | 0 | 0.02 |
| Formulation 2 | 0.3 | 0.55 | >3.19 | 0 | 0.38 |
| | 1.0 | >3.18 | >3.19 | 0.22 | 0.85 |
| Formulation 3 | 0.3 | >3.18 | >3.19 | 0.31 | 0.54 |
| | 1.0 | >3.18 | >3.19 | 1.56 | 4.02 |
| Formulation 4 | 0.3 | 3.18 | 3.19 | 0.39 | 0.87 |
| | 1.0 | 3.18 | 3.19 | 1.34 | >4.02 |

AWK = concentration used; RF values = germ reduction in LOG stages

What is claimed is:

1. An antimicrobial composition for the cleaning and disinfection of surfaces containing at least one peracid ester corresponding to the following general formula:

$$R\text{—}O_2C\text{—}(CH_2)_x\text{—}CO_3H$$

where R is an alkyl group containing 1 to 4 carbon atoms and x is a number from 1 to 4, combined with a component selected from
   (a) at least one fatty acid containing 8 to 18 carbon atoms and
   (b) at least one surface-active foam carrier component comprising an amine oxide derivative stable to oxidizing agent.

2. An antimicrobial synergistically acting composition as claimed in claim 1, wherein fatty acid a) contains 8 to 12 carbon atoms in the molecule.

3. A composition as claimed in claim 1, wherein the composition, based on the composition as a whole, contains 0.0001 to 15% by weight of a peracid ester and
   a) 0.01 to 15% by weight of at least one fatty acid containing 8 to 18 carbon atoms and
   b) 0.01 to 15% by weight of at least one surface-active foam carrier component.

* * * * *